United States Patent
Lewis et al.

(10) Patent No.: US 8,221,487 B2
(45) Date of Patent: *Jul. 17, 2012

(54) INTRALUMINAL STENT GRAFT

(75) Inventors: James D. Lewis, Flagstaff, AZ (US);
David J. Myers, Camp Verde, AZ (US);
Wayne D. House, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/781,358

(22) Filed: May 17, 2010

(65) Prior Publication Data
US 2010/0217375 A1    Aug. 26, 2010

Related U.S. Application Data

(60) Continuation of application No. 12/695,247, filed on Jan. 28, 2010, now Pat. No. 8,080,051, which is a continuation of application No. 11/237,587, filed on Sep. 27, 2005, now Pat. No. 7,691,141, which is a continuation of application No. 10/413,731, filed on Apr. 14, 2003, now Pat. No. 6,949,119, which is a continuation of application No. 10/083,461, filed on Feb. 25, 2002, now Pat. No. 6,547,815, which is a continuation of application No. 09/306,522, filed on May 6, 1999, now Pat. No. 6,357,104, which is a division of application No. 08/872,837, filed on Jun. 11, 1997, now Pat. No. 5,925,075, which is a continuation of application No. 08/109,214, filed on Aug. 18, 1993, now Pat. No. 5,735,892.

(51) Int. Cl.
*A61M 29/00*    (2006.01)

(52) U.S. Cl. ...................................................... 623/1.13
(58) Field of Classification Search .......... 606/191–198; 623/1.11, 1.13, 1.123, 1.25, 1.36, 1.46
See application file for complete search history.

(56) References Cited

U.S. PATENT DOCUMENTS

| | | |
|---|---|---|
| 3,657,744 A | 4/1972 | Ersek |
| 3,868,956 A | 3/1975 | Alfidi et al. |
| 3,953,566 A | 4/1976 | Gore |
| 4,130,904 A | 12/1978 | Whalen |
| 4,140,126 A | 2/1979 | Choudury |

(Continued)

FOREIGN PATENT DOCUMENTS

DE    3918736    12/1990

(Continued)

OTHER PUBLICATIONS

Balko A et al. Transfemoral Placement of Intraluminal Polyurethane Prosthesis for Abdominal Aortic Aneurysm. J of Surg Research 1986; 40:305-309.

(Continued)

*Primary Examiner* — Kevin T Truong
(74) *Attorney, Agent, or Firm* — Gilbert R. Gabo

(57) ABSTRACT

A method of making an tubular intraluminal graft in the form of a tubular diametrically adjustable stent having a tubular covering of porous expanded PTFE which is less than 0.10 mm thick. The covering may be on the exterior surface of the stent, or on the interior surface of the stent, or both. The covering may be affixed to the stent by an adhesive which is preferably fluorinated ethylene propylene.

10 Claims, 4 Drawing Sheets

U.S. PATENT DOCUMENTS

| | | | |
|---|---|---|---|
| 4,190,909 A | 3/1980 | Ablaza | |
| 4,283,448 A | 8/1981 | Bowman | |
| 4,300,244 A | 11/1981 | Bokros | |
| 4,304,010 A | 12/1981 | Mano | |
| 4,313,231 A | 2/1982 | Koyamada | |
| 4,385,093 A | 5/1983 | Hubis | |
| 4,478,898 A | 10/1984 | Kato | |
| 4,512,338 A | 4/1985 | Balko et al. | |
| 4,553,545 A | 11/1985 | Maass et al. | |
| 4,562,596 A | 1/1986 | Kornberg | |
| 4,577,631 A | 3/1986 | Kreamer | |
| 4,580,568 A | 4/1986 | Gianturco | |
| 4,655,771 A | 4/1987 | Wallsten | |
| 4,681,110 A | 7/1987 | Wiktor | |
| 4,728,328 A | 3/1988 | Hughes et al. | |
| 4,740,207 A | 4/1988 | Kreamer | |
| 4,776,337 A | 10/1988 | Palmaz | |
| 4,787,899 A | 11/1988 | Lazarus | |
| 4,791,966 A | 12/1988 | Eilentropp | |
| 4,820,298 A | 4/1989 | Leveen et al. | |
| 4,877,030 A | 10/1989 | Beck et al. | |
| 4,878,906 A | 11/1989 | Lindemann et al. | |
| 4,925,710 A | 5/1990 | Buck et al. | |
| 4,954,126 A | 9/1990 | Wallsten | |
| 5,078,726 A | 1/1992 | Kreamer | |
| 5,078,736 A | 1/1992 | Behl | |
| 5,089,006 A | 2/1992 | Stiles | |
| 5,107,852 A | 4/1992 | Davidson et al. | |
| 5,122,154 A | 6/1992 | Rhodes | |
| 5,123,917 A * | 6/1992 | Lee | 623/22.26 |
| 5,147,370 A | 9/1992 | McNamara et al. | |
| 5,151,105 A | 9/1992 | Kwan-Gett | |
| 5,156,620 A | 10/1992 | Pigott | |
| 5,163,955 A | 11/1992 | Love et al. | |
| 5,211,658 A * | 5/1993 | Clouse | 623/1.14 |
| 5,225,131 A | 7/1993 | Tamaru et al. | |
| 5,236,447 A | 8/1993 | Kubo et al. | |
| 5,254,113 A | 10/1993 | Wilk | |
| 5,258,023 A | 11/1993 | Reger | |
| 5,282,823 A | 2/1994 | Schwartz et al. | |
| 5,282,824 A | 2/1994 | Gianturco | |
| 5,344,426 A | 9/1994 | Lau et al. | |
| 5,405,377 A | 4/1995 | Cragg | |
| 5,441,515 A | 8/1995 | Khosravi et al. | |
| 5,443,499 A | 8/1995 | Schmitt | |
| 5,507,767 A | 4/1996 | Maeda et al. | |
| 5,556,414 A | 9/1996 | Turi | |
| 5,637,113 A | 6/1997 | Tartaglia et al. | |
| 5,645,559 A | 7/1997 | Hachtman et al. | |
| 5,700,285 A | 12/1997 | Myers et al. | |
| 5,735,892 A | 4/1998 | Myers et al. | |
| 5,810,870 A | 9/1998 | Myers et al. | |
| 5,876,448 A | 3/1999 | Thompson et al. | |
| 6,165,212 A | 12/2000 | Dereme et al. | |
| 6,174,329 B1 | 1/2001 | Callol et al. | |

FOREIGN PATENT DOCUMENTS

| | | |
|---|---|---|
| EP | 10293 | 4/1980 |
| EP | 461791 | 12/1991 |
| EP | 464755 | 1/1992 |
| EP | 466518 | 1/1992 |
| EP | 480667 | 4/1992 |
| EP | 508473 | 10/1992 |
| EP | 518704 | 12/1992 |
| EP | 528039 | 2/1993 |
| EP | 539237 | 4/1993 |
| EP | 551179 | 7/1993 |
| EP | 814729 | 9/1995 |
| JP | 5536492 | 5/1976 |
| JP | 5367109 | 6/1978 |
| JP | 60172306 | 9/1985 |
| WO | 8704935 | 8/1987 |
| WO | 9112779 | 9/1991 |
| WO | 9113648 | 9/1991 |

OTHER PUBLICATIONS

Carrel A Results of the permanent intubation of the thoracic aorta. Surg., Gyn and Ob. 1912;15:245-248.

Chuter TAM, et al. Transfemoral Endovascular Aortic Graft Placement. J Vas Surg 1993; 18(2):185-197.

Cragg AH, Drake MD Percutaneous Femoropopliteal Graft Placement. Radiology 1993; 187(3):643-648.

George PJM et al. Covered expandable metal stent for recurrent tracheal obstruction. The Lancet 1990; 335:582-584.

Kato M et al. Development of a chronic endothelialized transcatheter implantable intra-aortic graft. ASAIO Journal 1993; M518-M521.

Lawrence DD et al. Percutaneous Endovascular Graft: Experimental Evaluation. Radiology 1987; 163.2 :357-360.

Mirich E et al. Percutaneously Placed Endovascular Grafts for Aortic Aneurysms; Feasibility Study. Radiology 1989; 170(3):1033-1037.

Parodi JC et al. Transfemoral Intraluminal Graft Implantation for Abdominal Aortic Aneurysms. Annals of Vasc Surg 1991; 5(6):491-499.

Preminger TJ et al. Transluminal vascular stenting using a GORE-TEX covered stent: An experimental study. Presented at the congress of Pediatric Cardiology and Cardiac Surgery Jun. 21-25, 1993.

Sayers RD et al. Endovascular stenting of abdominal aortic aneurysms. Eur J Vasc Surg 1993; 7:225-227.

Schenck RR and Derman GH An Intraluminal Silastic Stent for Small Vessel Repair. Orth Clin North Amer 1997; 8(2):265-271.

Yoshida H et al. Transcatheter Placement of an Intraluminal Prosthesis for the Thoracic Aorta, A New Approach to Aortic Dissections. ASAIO Transactions 1991; 37:M272-M273.

The Journal of Teflon, Sep.-Nov. 1971, vol. 12, No. 3, pp. 2-4.

US District Court for Eastern District of Virginia, Norfolk Division; Case No. 2:10-cv-00441-MSD-DEM. Case docket. Jan. 23, 2012; 26 pages.

US District Court for Eastern District of Virginia, Norfolk Division; Case No. 2:10-cv-00441-MSD-DEM. Berry Expert report and exhibits. Jan. 6, 2012; 518 pages.

US District Court for Eastern District of Virginia, Norfolk Division; Case No. 2:10-cv-00441-MSD-DEM. Claim Construction- Opinion and Order. Dec. 14, 2011; 44 pages.

US District Court for Eastern District of Virginia, Norfolk Division; Case No. 2:10-cv-00441-MSD-DEM. Loomis supp report and exhibits. Dec. 23, 2011; 704 pages.

US District Court for Eastern District of Virginia, Norfolk Division; Case No. 2:10-cv-00441-MSD-DEM. Veith Opening report and exhibits. Nov. 21, 2011; 315 pages.

US District Court for Eastern District of Virginia, Norfolk Division; Case No. 2:10-cv-00441-MSD-DEM. Veith rebuttal report. Nov. 21, 2011; 134 pages.

US District Court for Eastern District of Virginia, Norfolk Division; Case No. 2:10-cv-00441-MSD-DEM. Zarins deposition excerpt. Jan. 19, 2012; 38 pages.

US District Court for Eastern District of Virginia, Norfolk Division; Case No. 2:10-cv-00441-MSD-DEM. Zarins report and exhibits. Jan. 6, 2012; 111 pages.

* cited by examiner

INTRALUMINAL STENT GRAFT

CROSS REFERENCE TO RELATED APPLICATIONS

This application is a continuation of U.S. application Ser. No. 12/695,247 filed Jan. 28, 2010, now U.S. Pat. No. 8,080,051, which is a continuation of U.S. application Ser. No. 11/237,587 filed Sep. 27, 2005, now U.S. Pat. No. 7,691,141, which is a continuation of U.S. application Ser. No. 10/413,731, filed Apr. 14, 2003 (U.S. Pat. No. 6,949,119), which is a continuation of U.S. application Ser. No. 10/083,461, filed Feb. 25, 2002 (U.S. Pat. No. 6,547,815), which is a continuation of U.S. application Ser. No. 09/306,522, filed May 6, 1999 (U.S. Pat. No. 6,357,104), which is a division of U.S. application Ser. No. 08/872,837, filed Jun. 11, 1997 (U.S. Pat. No. 5,925,075), which is a continuation of U.S. application Ser. No. 08/109,214, filed Aug. 18, 1993 (U.S. Pat. No. 5,735,892).

FIELD OF THE INVENTION

This invention relates to the field of intraluminal grafts and particularly to a method of making thin-wall intraluminal grafts useful as an inner lining for blood vessels or other body conduits.

BACKGROUND OF THE INVENTION

Conventional vascular grafts have long been used for vascular repair in humans and animals. These devices are typically flexible tubes of woven or knitted polyethylene terephthalate or of porous polytetrafluoroethylene (hereinafter PTFE). Grafts of biological origin are also used, these being typically fixed human umbilical or bovine arteries. These conventional vascular grafts usually require invasive surgical methods that expose at least both ends of the segment of vessel to be repaired. Frequently it is necessary to expose the entire length of the vessel segment. These types of repairs consequently cause major trauma to the patient with corresponding lengthy recovery periods and may result in occasional mortality.

Alternative methods have evolved which use intraluminal vascular grafts in the form of adjustable stent structural supports, tubular grafts or a combination of both. These devices are preferably remotely introduced into a body cavity by the use of a catheter type of delivery system. Alternatively they may be directly implanted by invasive surgery. The intent of these methods is to maintain patency after an occluded vessel has been re-opened using balloon angioplasty, laser angioplasty, atherectomy, roto-ablation, invasive surgery, or a combination of these treatments.

Intraluminal vascular grafts can also be used to repair aneurysmal vessels, particularly aortic arteries, by inserting an intraluminal vascular graft within the aneurysmal vessel so that the prosthetic withstands the blood pressure forces responsible for creating the aneurysm.

Intraluminal vascular grafts provide a new blood contacting surface within the lumen of a diseased living vessel. Intraluminal grafts are not, however, limited to blood vessels; other applications include urinary tracts, biliary ducts, respiratory tracts and the like.

If the intraluminal graft used is of thin enough wall and adequate flexibility, it may be collapsed and inserted into a body conduit at a smaller diameter location remote from the intended repair site. A catheter type of delivery system is then used to move the intraluminal graft into the repair site and then expand its diameter appropriately to conform to the inner surface of the living vessel. Various attachment methods including the use of adjustable stents may be used to secure the intraluminal graft at the desired location without the necessity of invasive surgery.

Intraluminal vascular grafts were suggested as early as 1912 in an article by Alexis Carrel (Results of the permanent intubation of the thoracic aorta. Surg., Gyn and Ob. 1912; 15:245-248). U.S. Pat. No. 3,657,744 to Ersek describes a method of using one or more adjustable stents to secure a flexible fabric vascular graft intraluminally, the graft and stent having been introduced distally and delivered to the desired position with a separate delivery system.

Choudhury, U.S. Pat. No. 4,140,126, describes a similar method of repairing aortic aneurysms whereby a polyethylene terephthalate vascular graft is fitted at its ends with metal anchoring pins and pleated longitudinally to collapse the graft to a size small enough to allow for distal introduction.

Rhodes, U.S. Pat. No. 5,122,154 and Lee, U.S. Pat. No. 5,123,917, describe endovascular bypass grafts for intraluminal use which comprise a sleeve having at least two diametrically-expandable stents. Rhodes teaches that the sleeve material is to be made of conventional vascular graft materials such as GORE-TEX® Vascular Graft (W. L. Gore & Associates, Inc., Flagstaff Ariz.) or Impra® Graft (Impra, Inc. Tempe Ariz.). Both the GORE-TEX Vascular Graft and Impra Graft are extruded and longitudinally expanded PTFE tubes. Additionally, the GORE-TEX Vascular Graft possesses an exterior helical wrapping of porous expanded PTFE film. The difficulty with the use of either the GORE-TEX Vascular Graft or the Impra graft as the sleeve component is that the relatively thick, bulky wall of the extruded, longitudinally expanded PTFE tubes limits the ability of the tube to be contracted into a small cross-sectional area for insertion into a blood vessel. For example, the wall thickness of a 6 mm inside diameter Thin Walled GORE-TEX Vascular Graft is typically 0.4 mm. The thinness of the wall is limited by the difficulty of manufacturing an extruded, longitudinally expanded tube having a thin wall of uniform thickness.

SUMMARY OF THE INVENTION

The present invention is a method of making a tubular intraluminal graft comprising a tubular, diametrically adjustable stent having an exterior surface, a luminal surface and a wall having a multiplicity of openings through the wall, and further having a tubular covering of porous expanded PTFE film affixed to the stent, said covering being less than about 0.10 mm thick.

Porous expanded PTFE film has a microstructure of nodes interconnected by fibrils and is made as taught by U.S. Pat. Nos. 3,953,566; 4,187,390 and 4,482,516. As will be described further, the fibrils may be uniaxially oriented, that is, oriented in primarily one direction, or multiaxially oriented, that is, oriented in more than one direction. The term expanded is used herein to refer to porous expanded PTFE. The terms expand, expanding and expandable are used herein to refer to diametrically adjustable intraluminal stents. More specifically, the term balloon-adjustable refers to stents of the Palmaz type as taught by U.S. Pat. No. 4,776,337 which typically require a balloon catheter to increase the diameter of the stent within a blood vessel. The term self-expanding refers to stents which increase in diameter by various other means. Stents of this type include stents of braided wire made as taught by Wallsten, U.S. Pat. No. 4,544,771; and stents of formed wire made as taught by Gianturco, U.S. Pat. No. 4,580,568. Stents of this type expand to a larger diameter after being released from a constraining force which restricts them to a smaller diameter. Self-expanding stents also include stents formed from Nitinol wire made as taught by PCT US 92/03481. These stents expand in diameter when exposed to a slight increase in temperature.

The tubular covering of porous expanded PTFE film may be affixed to either the exterior surface or the luminal surface of the stent. Alternatively, a first tubular covering of porous expanded PTFE film may be affixed to the exterior surface of the tubular diametrically adjustable stent and a second tubular covering of porous expanded PTFE film may be affixed to the luminal surface of the tubular diametrically adjustable stent. The first and second tubular coverings of porous expanded PTFE film may be affixed to each other through the openings through the wall of the stent.

The porous expanded PTFE film may be affixed to the stent with an adhesive. The adhesive may be a thermoplastic adhesive and more preferably a thermoplastic fluoropolymer adhesive such as fluorinated ethylene propylene (hereinafter FEP) or perfluoroalkoxy (hereinafter PFA). Where first and second tubular coverings of expanded PTFE film are affixed to each other through the multiplicity of openings in the stent wall, the two coverings may be affixed by heating them above the crystalline melt point of the PTFE film adequately to cause them to thermally adhere, or alternatively they may be affixed by an adhesive such as FEP.

DETAILED DESCRIPTION OF THE INVENTION

Figure 1:
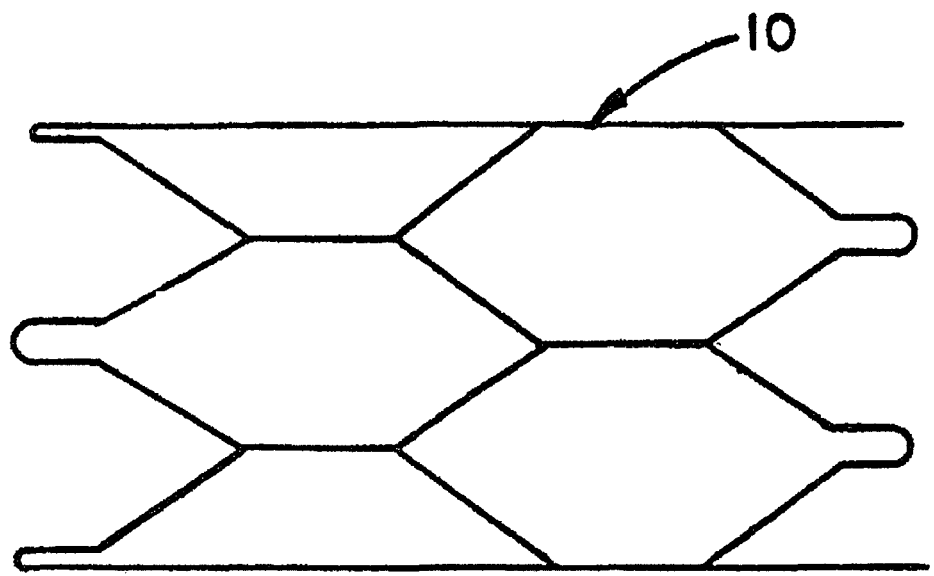
FIG. 1 is a side view of a typical diametrically adjustable stent.

FIG. 1 is a side view of a typical diametrically adjustable stent. The stent is shown as it would appear implanted into a body conduit with its diameter adjusted beyond the collapsed pre-implantation diameter. While the stent shown is made from metal wire, a perforated sleeve having perforations of suitable shape, size and quantity may also be used. Various suitable stents are described by U.S. Pat. No. 4,776,337 to Palmaz and PCT US 92/03481 to Hess. These stents may be made from implantable metals such as titanium, stainless steel, or Nitinol.

The stent may be provided with an exterior covering of porous expanded PTFE film, or a luminal covering of porous expanded PTFE film, or with both exterior and luminal coverings. Uniaxially-oriented films having a microstructure of uniaxially-oriented fibrils wherein substantially all of the fibrils are oriented parallel to each other may be used. Multiaxially-oriented films having a microstructure of biaxially or multiaxially-oriented fibrils wherein the fibrils are oriented in at least two directions which are substantially perpendicular to each other may also be used.

Figure 2:
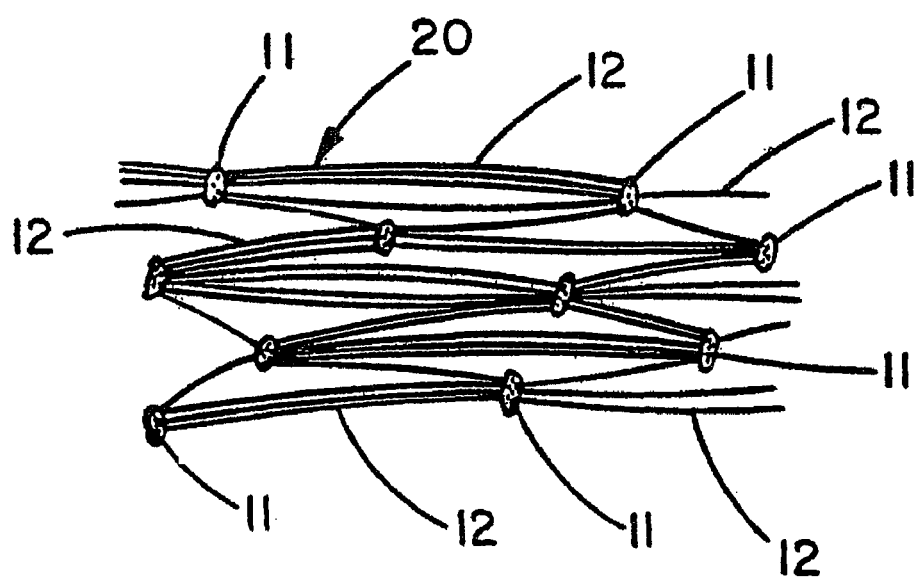
FIG. 2 is an enlarged schematic representation of the microstructure of porous expanded PTFE film having a microstructure with uniaxially-oriented fibrils as used to construct Examples 1 and 3.
Figure 3A:
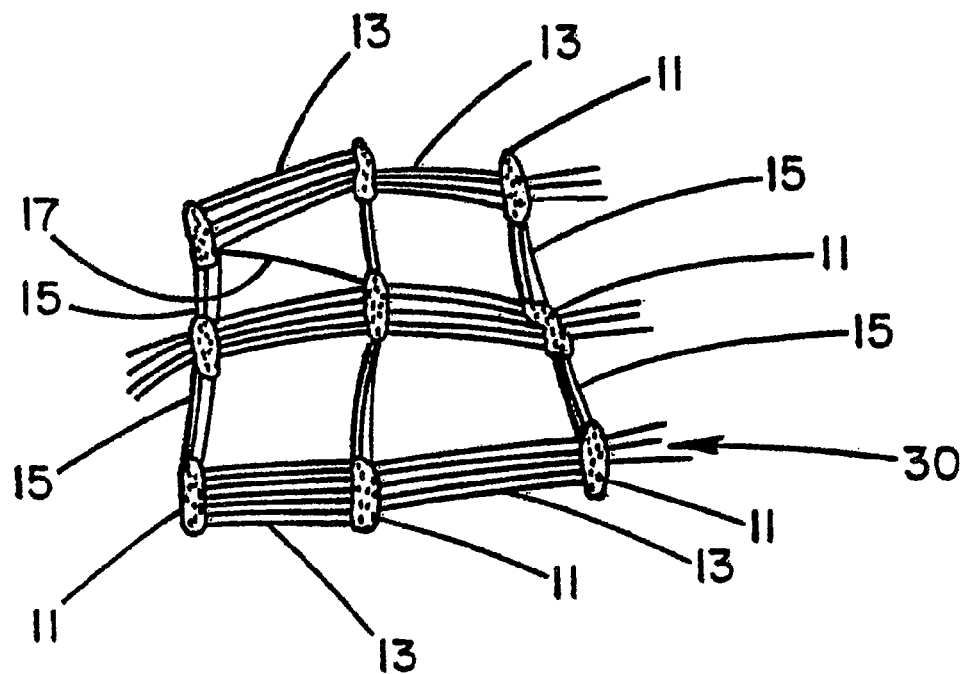
FIGS. 3A and 3B describe enlarged schematic representations of the microstructure of porous expanded PTFE film having microstructures of multiaxially-oriented fibrils as used to construct Example 2.
Figure 3B:
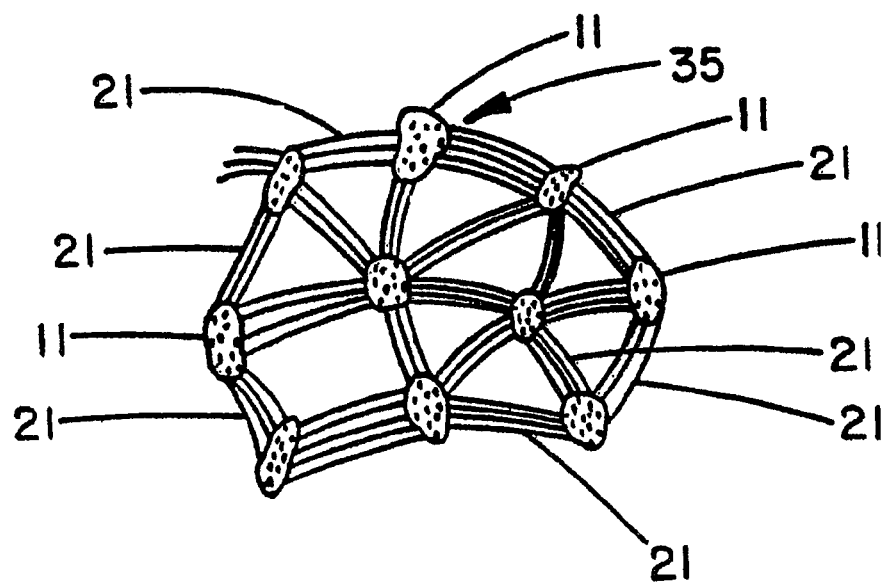

FIG. 2 describes an enlarged schematic representation of the microstructure of nodes 11 connected by fibrils 12 of a film 20 wherein the uniaxially-oriented fibrils 12 are substantially parallel to each other. FIGS. 3A and 3B describe enlarged schematic representations of alternative microstructures of porous expanded PTFE films that may also be used for making the present invention. These microstructures have nodes interconnected by fibrils wherein the fibrils are oriented in at least two directions which are substantially perpendicular to each other. FIG. 3A describes a microstructure 30 of nodes 11 and fibrils 13 and 15 wherein the fibrils 13 and 15 are biaxially-oriented fibrils which are oriented in two different directions that are substantially perpendicular to each other. Those microstructures may contain some fibrils 17 which are not oriented in the two different directions. FIG. 3B describes another alternative microstructure 35 wherein the fibrils 21 are multiaxially-oriented fibrils oriented in virtually all directions within the plane of the sheet material. Either of these films may be made by having been expanded two directions that are perpendicular to each other. The microstructure 30 of multiaxially-oriented fibrils 21 may also have been made by being expanded in more than two directions as shown by FIG. 3B. The manufacture of these films is taught by U.S. Pat. Nos. 3,953,566; 4,198,390 and 4,482,516.

The fibril lengths of the porous expanded PTFE films referred to herein were estimated mean values obtained by examining scanning electron photomicrographs of these films. For multiaxially-oriented films, these estimates included consideration of fibrils oriented in all directions. The mean fibril lengths of the films used to construct the intraluminal grafts of the present invention are preferred to be within the range of about 5 to about 120 microns, although fibril lengths beyond this range may also be useful.

Wall thickness measurements of intraluminal graft stent coverings were determined by cutting away a portion of the covering that covered an opening through the stent wall. The thickness of the sample portion was measured by placing the sample portion between the pads of a Mitutoyo model no. 804-10 snap gauge having a part no. 7300 frame, and gently easing the pads into contact with the sample portion until the pads were in full contact with the sample portion under the full force of the spring-driven snap gauge pads. Film density measurements were based on the bulk volume of a film sample using the snap-gauge thickness measurement.

The following examples of intraluminal stent grafts are intended to be illustrative only and are not intended to limit the scope of the invention to only the constructions described by these examples.

Example 1

A Nitinol wire stent 10 (Nitinol Medical Technologies, Boston, Mass.) of the type described by FIG. 1 was provided with both a luminal covering and an exterior covering of expanded PTFE film. This 3 cm long stent was formed from 0.25 mm diameter Nitinol wire into a tubular shape of interlocking hexagons. The luminal and exterior coverings were both made from a uniaxially-oriented film having fibrils oriented substantially in a single direction wherein the fibrils were all substantially parallel to each other. The luminal covering was provided with the fibrils oriented parallel to the longitudinal axis of the tubular stent; the exterior covering was provided with the fibrils oriented substantially circumferential to the tubular stent. The film used for both the luminal and exterior coverings was a porous expanded PTFE film having a discontinuous, porous coating of FEP applied to one side of the porous expanded PTFE film. Examination of the FEP coated side of the film by scanning electron microscopy revealed FEP on only small portions of the nodes and fibrils at the surface of the film. It was estimated that less than 10% of the available node and fibril surface area exposed at the surface of the film was covered by FEP. The presence of the FEP adhesive thus had little or no adverse effect on the porosity of the porous PTFE film.

The FEP-coated porous expanded. PTFE film was made by a process which comprises the steps of:

a) contacting a porous PTFE film with another layer which is preferably a film of FEP or alternatively of another thermoplastic polymer;
b) heating the composition obtained in step a) to a temperature above the melting point of the thermoplastic polymer;
c) stretching the heated composition of step b) while maintaining the temperature above the melting point of the thermoplastic polymer; and
d) cooling the product of step c).

In addition to FEP, other thermoplastic polymers including thermoplastic fluoropolymers may also be used to make this coated film. The adhesive coating on the porous expanded PTFE film may be either continuous (non-porous) or discontinuous (porous) depending primarily on the amount and rate of stretching, the temperature during stretching, and the thickness of the adhesive prior to stretching.

The discontinuously FEP-coated porous expanded PTFE film used to construct this example was of about 0.01 mm thickness and had a density of about 0.3 g/cc. The microstructure of the porous expanded PTFE contained fibrils of about 50 micron mean fibril length.

Figure 4:
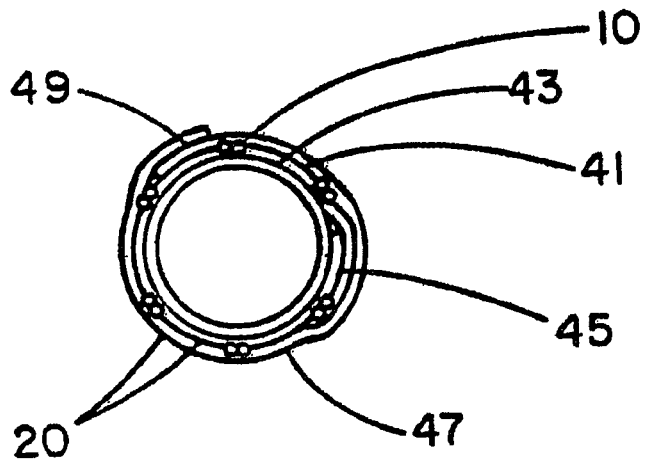
FIG. 4 is a transverse cross section of the stent of Example 1 having a luminal layer of porous expanded PTFE film with longitudinally-oriented fibrils and an exterior layer of porous expanded PTFE film with circumferentially-oriented fibrils.

A 3.0 cm length of film 20 having uniaxially-oriented fibrils was wrapped as a single layer 41 around a hollow, tubular, 1.5 cm outside diameter mandrel 43 of non-porous PTFE to form a seam 45 as described by the cross section of FIG. 4. The seam edges 45 overlapped as shown by about 3 mm. The fibrils of the film were oriented parallel to the longitudinal axis of the mandrel; the FEP-coated side of the film faced away from the surface of the mandrel. The Nitinol stent was carefully fitted over the film-wrapped portion of the mandrel. The 3 cm length of the stent was centered over the 3.0 cm length of film-wrapped mandrel. The stent was then provided with an exterior covering 47 of a 3.0 cm wide tape of the film described above by wrapping the tape circumferentially around the exterior surface of the mandrel so that the edges of the circumferentially-wrapped tape overlapped by about 3 mm to form seam 49. The circumferentially wrapped covering was oriented so that the FEP-coated side of the tape faced inward in contact with the exterior surface of the stent and the outward facing FEP-coated surface of the luminal layer of film exposed through the openings in the stent. Except for the overlapped seam edges 49, the circumferentially-wrapped covering was only one film layer thick. The uniaxially-oriented fibrils of the microstructure of the circumferentially-wrapped tape were circumferentially-oriented about the exterior stent surface.

The film-wrapped mandrel assembly was placed into an oven set at 360° C. for a period of 4 minutes after which the film-wrapped mandrel was removed from the oven and allowed to cool. Following cooling to approximately ambient temperature, the mandrel was removed from the film-wrapped stent. The amount of heat applied was adequate to melt the FEP-coating on the porous expanded PTFE film and thereby cause adjacent layers of film to adhere to each other. Thus the luminal layer of film was adhered to the exterior circumferentially wrapped layer through the openings between the adjacent wires of the stent. The combined thickness of the luminal and exterior coverings was about 0.025 mm.

The film-covered stent was then chilled in a bath of ice water while being rolled between human fingers applying compression diametrically across the stent. This reduced the outside diameter of the stent to about 0.3 cm. The collapsed stent was then heated by immersion in about 40° C. water, thereby increasing the stent diameter to about 1.5 cm. The film covering showed no visible adverse effects from the process of shrinking and increasing the stent diameter.

Example 2

A Nitinol wire stent of the same type used for Example 1 was provided with a luminal covering of a porous expanded PTFE film having a microstructure of biaxially-oriented fibrils as shown by FIG. 3A. This was accomplished by wrapping a hollow tubular mandrel of non-porous PTFE with a layer of porous expanded PTFE film having a continuous (non-porous) coating of FEP with the FEP-coated side of the film facing outwardly away from the mandrel surface. This film was about 0.02 mm thick; the porous expanded PTFE had a microstructure of uniaxially-oriented fibrils with the fibrils oriented circumferentially about the exterior surface of the mandrel. The Nitinol stent was carefully fitted over the film-wrapped portion of the mandrel. The mandrel assembly was then placed into an oven set at 360° C. for four minutes. After removal from the oven and subsequent cooling, the mandrel was removed from the stent leaving the wrapped film adhered to the luminal surface of the stent. This film was then peeled from the luminal stent surface, leaving the FEP-coating and some small shreds of residual porous expanded PTFE adhered to the luminal surface of the stent wires. By removing the film and leaving the FEP adhesive on the luminal stent surface, the film served only as a release substrate for the application of the adhesive to the stent surface.

Figure 5:
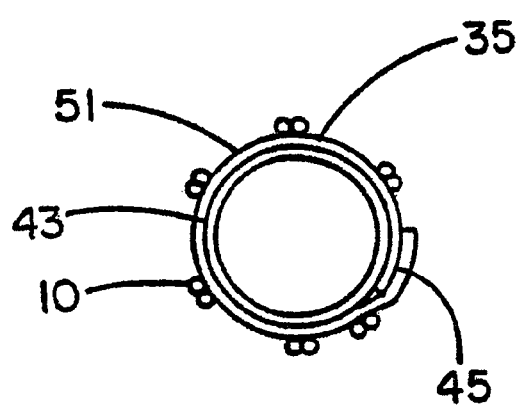
FIG. 5 is a transverse cross section of the stent of Example 2 having a luminal layer of porous expanded PTFE film with biaxially-oriented fibrils.

As shown by FIG. 5, the mandrel 43 was then provided with a single layer 51 wrapping of a porous expanded PTFE film 35 having a microstructure of biaxially-oriented fibrils. This film was of about 30 micron fibril length, about 0.08 mm thickness, about 0.3 g/cc density and did not have an FEP coating. The biaxially-oriented fibrils were oriented to be substantially parallel to the longitudinal axis of the mandrel and to the circumference of the mandrel.

The film was overlapped adequately to form a 2 mm wide, longitudinally oriented seamline 45 parallel to the longitudinal axis of the mandrel. A sheet of polyamide film was temporarily placed over the surface of the seam and then contacted with the surface of a hand-held iron set at 400° C. to cause the PTFE film seam edges to adhere to each other. Excess material beyond the 2 mm wide seam was trimmed away and discarded. The stent was again carefully fitted over the film-covered mandrel. The resulting assembly was placed into an oven set at 380° C. for three minutes and then removed and allowed to cool, after which the mandrel was removed from the stent. The porous expanded PTFE film appeared to be well adhered to the luminal surface of the wire stent by the FEP coating left from the first, previously removed, layer of film. The wall thickness of the PTFE film covering was about 0.08 mm.

The film-covered stent was then chilled in a bath of ice water while being rolled between human fingers applying compression diametrically across the stent. This reduced the outside diameter of the stent to about 0.3 cm. The collapsed stent was then heated by immersion in about 40° C. water, thereby increasing the stent diameter to about 1.5 cm. The film covering showed no visible adverse effects from the process of shrinking and increasing the stent diameter.

Example 3

Figure 6:
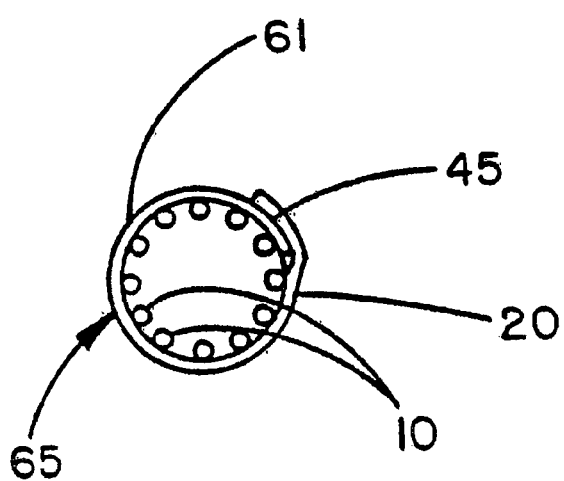
FIG. 6 is a transverse cross section of the stent of Example 3 having an exterior layer of porous expanded PTFE film with circumferentially-oriented fibrils.

A Palmaz stent of the balloon-expandable type (part no. PS30, Johnson & Johnson Interventional Systems, Inc., Warren, N.J.) was adjusted from its collapsed outside diameter of 3.4 mm to an enlarged outside diameter of 8.0 mm by inserting a tapered stainless steel mandrel followed by a straight 8.0 mm diameter stainless steel mandrel. This stent was then provided with a single layer exterior wrapping of the same discontinuously FEP-coated porous expanded PTFE coating used for the exterior wrapping of the stent of Example 1. This was accomplished by wrapping the film about the exterior surface of the mandrel with the uniaxially-oriented fibrils of the film microstructure oriented parallel to the longitudinal axis of the stent. This exterior covering 61 is described by the transverse cross section of FIG. 6. A 2 mm wide seam 45 was formed from the overlapped edges of the porous expanded PTFE film 20 by temporarily placing a thin sheet of polyamide film over these edges and applying heat from a hand-held iron with a surface temperature of about 400° C. The film-wrapped stent 65 was then placed into an oven set at 380° C. for 3 minutes, after which it was removed and allowed to cool. The film appeared to be well adhered to the exterior surface of the stent. The wall thickness of the film covering was about 0.01 mm. The enlarged stent was then collapsed by the following process.

Figure 7:
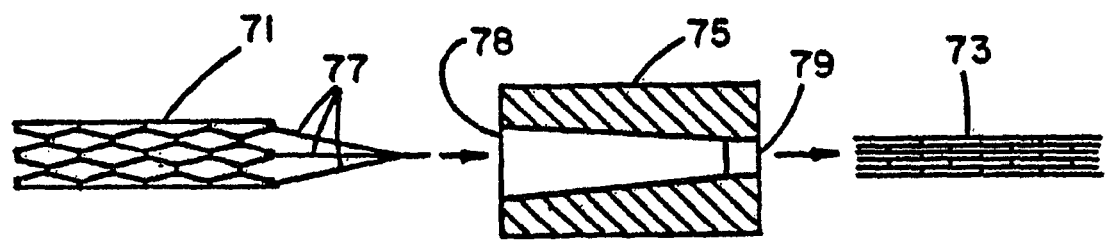
FIG. 7 describes a method of collapsing a previously outwardly adjusted balloon-expandable stent.

A series of 20 cm long 6-0 sutures were tied individually to each of the closed metal stent openings adjacent to one end of a stent. The film-covered stent was provided with a temporary non-adhered additional wrapping of longitudinally-oriented film without FEP and having a microstructure of uniaxially-oriented fibrils. This temporary wrapping was intended as a dry lubricant. As described by FIG. 7 which omits the exterior film covering for clarity, the enlarged stent 71 was then pulled by these sutures 77 through a tapered die 75 of round cross section and 2.5 cm length, the die having a tapered orifice with a 9.5 mm diameter bore at its entrance 78 and a 4.5 mm diameter bore at its exit 79. The result was that the stent was collapsed back to an outside diameter of 4.5 mm. The lubricity of the temporary covering of porous expanded PTFE film aided in making it possible to pull the stent through the die. This temporary covering was removed after completion of the collapsing process. It is anticipated that the use of a tapered die having an appropriately sized, smaller diameter exit bore would result in collapsing the stent to its original collapsed diameter. The film-covered stent was again enlarged to a diameter of 8 mm using a balloon catheter followed by a tapered stainless steel mandrel. The covering of porous expanded PTFE film appeared to be fully intact after the collapsing and enlarging of the film-covered stent.

Figure 8:
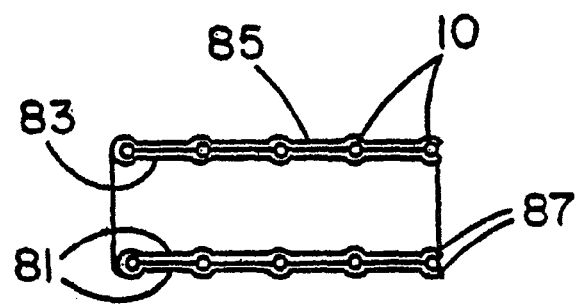
FIG. 8 describes the fitting of a single tubular sleeve to both the exterior and luminal surfaces of a stent.

Stent coverings may be affixed to a stent surface by variations on this method. For example, a tubular sleeve may be made from a film of porous expanded PTFE and inverted back into itself and fitted over the inner and outer surfaces of a stent as shown by FIG. 8. The inner 83 and outer 85 portions of the tubular sleeve 81 may be thermally adhered to each other through the openings in the stent wall, or may be adhered to the stent surfaces by an adhesive such as FEP, or may be affixed to the stent by suturing the open ends 87 of the tube together.

Example 4

A long length of 0.07 mm diameter single strand 304 stainless steel wire was provided with a single layer, approximate 1 mm overlap covering of porous expanded PTFE film by helically wrapping the wire with a narrow tape cut from a sheet of porous expanded PTFE film. The tape used was 6 mm wide, 0.01 mm thick, 0.3 g/cc density, and had uniaxially-oriented fibrils of about 50 micron fibril length. This tape-covered wire was then heated by pulling the wire through the 0.14 mm diameter orifice of a 2.5 cm long die heated to 400° C., at a rate of 1.5 meters per minute, thereby adhering the overlapped edges of the tape together and thereby adhering the tape to the wire. This wire was then cut into shorter lengths and spooled onto 16 bobbins. These bobbins were used to supply the wire to a model D-5600 Steeger braider.

Figure 9:
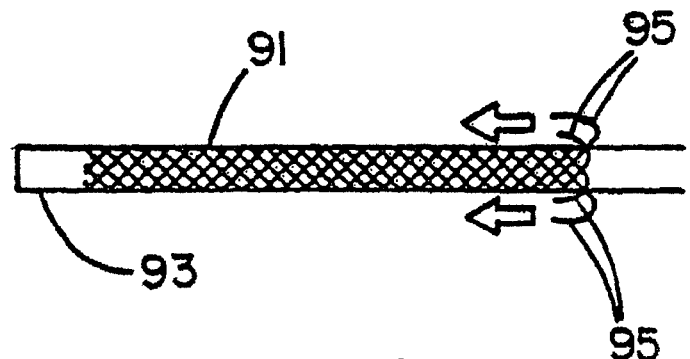
FIG. 9 describes the removal a covered, braided wire stent of the self-expanding type from a manufacturing mandrel by everting the braided wire, thereby placing the covering on the luminal surface of the stent.

A 12 meter length of 1.75 mm diameter non-porous PTFE mandrel was then fed into the braider where a braided covering of the above wire was applied at a density of about 16 picks/cm. An additional covering of tape cut from a sheet of porous expanded PTFE film was then helically wrapped over the surface of the wire-braided PTFE mandrel. The tape used for this helical wrapping was of 0.01 mm thickness, 0.3 g/cc density, about 50 micron fibril length and 12 mm width. Adjacent edges of the helical wrapping were overlapped by approximately 1 mm. The wire-braided Teflon mandrel was then placed into an oven set at 380° C. for four minutes, after which it was removed and allowed to cool. As shown by FIG. 9, the wire-braided stent 91 with the exterior covering of porous expanded PTFE tape was then removed from the non-porous PTFE mandrel 93 by folding the ends 95 of the braided wires back on themselves and pulling on these everted ends. The exterior covering of porous expanded PTFE film is omitted from FIG. 9 for clarity. By applying tension on these everted ends in a direction parallel to the longitudinal axis of the mandrel and from the everted end back toward the opposite, non-everted end, the entire braided construction was everted and simultaneously removed from the mandrel. This everting process of removing the braided assembly from the mandrel resulted in the helical wrapping of film being located on the lumen of the stent. This construction offered good self-expanding characteristics in that when longitudinal tension was placed on the stent, the length of the stent increased and the diameter decreased. Upon release of tension, the stent immediately recovered its previous shorter length and larger diameter. This film-covered stent is therefore expected to be useful as a self-expanding stent.

The invention claimed is:

1. An intraluminal graft comprising:
   a) a diametrically adjustable stent having an exterior surface, a luminal surface and a wall, the wall having a multiplicity of openings;
   b) a first covering adjacent to the luminal surface of the stent; and
   c) a second covering adjacent to the exterior surface of the stent and affixed to the first covering through the wall of the stent, wherein the second covering adjacent to the exterior surface of the stent is affixed to the first covering through the multiplicity of openings through the wall of the stent.

2. The intraluminal graft of claim 1 wherein the second covering is less than about 0.10 mm thick.

3. The intraluminal graft of claim 1 wherein the polymer forming the first covering is PTFE.

4. The intraluminal graft of claim 1 wherein the polymer forming the second covering is PTFE.

5. The intraluminal graft of claim 1 wherein the diametrically adjustable stent is a self-expanding stent.

6. The intraluminal graft of claim 1, wherein the diametrically adjustable stent is a Nitinol stent.

7. The intraluminal graft of claim 1, wherein the first or second covering is of porous expanded PTFE.

8. The intraluminal graft of claim 1, wherein the second covering adjacent to the exterior surface of the stent is affixed to the first covering through the multiplicity of openings through the wall of the stent via adhesive.

9. The intraluminal graft of claim 1, wherein the second covering adjacent to the exterior surface of the stent is affixed to the first covering through the multiplicity of openings through the wall of the stent via sutures.

10. The intraluminal graft of claim 1 wherein the combined thickness of the first and second coverings is less than about 0.05 mm thick.

* * * * *